United States Patent [19]
Crawford et al.

[11] Patent Number: 5,170,346
[45] Date of Patent: Dec. 8, 1992

[54] METHOD FOR REDUCING PATIENT TRANSLATION ARTIFACTS IN TOMOGRAPHIC IMAGING

[75] Inventors: Carl R. Crawford, Milwaukee; Kevin F. King, New Berlin, both of Wis.

[73] Assignee: General Electric Company, Milwaukee, Wis.

[21] Appl. No.: 440,531

[22] Filed: Nov. 22, 1989

[51] Int. Cl.⁵ .............................. G06F 15/00
[52] U.S. Cl. ................. 364/413.16; 378/14
[58] Field of Search ........... 364/413.15, 413.16, 364/413.17; 378/13, 14, 15

[56] References Cited

U.S. PATENT DOCUMENTS 4,580,219  4/1986  Pelc et al. ............ 364/413.15
4,630,202 12/1986  Mori .................... 364/413.15
4,789,929 12/1988  Nishimura et al. ..... 364/413.15

Primary Examiner—Roy N. Envall, Jr.
Assistant Examiner—Laura Brutman
Attorney, Agent, or Firm—Quarles & Brady

[57] ABSTRACT

A method of reducing artifacts in images acquired with fan beam, helical scanning, tomographic imaging systems, applies a weighting function to the tomographic projection set. The weighting function reduces the contribution to the final image of projection data with large helical offset. Other redundant data within the projection set is increased in weight by the weighting function to prevent image artifacts from the weighting. In one embodiment, the projection set is centered on the slice plane to avoid discontinuities in the projection data caused by the weighting functions.

7 Claims, 6 Drawing Sheets

METHOD FOR REDUCING PATIENT TRANSLATION ARTIFACTS IN TOMOGRAPHIC IMAGING

BACKGROUND OF THE INVENTION

This invention relates to computed tomography using helical scanning. More specifically, the invention relates to an image reconstruction method for reducing image artifacts that result from the translation of the patient during the helical scan.

As used herein, computed tomography shall refer to both tomography using "transmission imaging" that is, detecting radiation transmitted through the body being imaged, and "emission imaging", detecting radiation emitted from the body being imaged, e.g., such as that being emitted by radiopharmaceutical isotopes.

In a transmission imaging computed tomography system, an x-ray source is collimated to form a fan beam with a defined fan beam angle. The fan beam is orientated to lie within the x-y plane of a Cartesian coordinate system, termed the "imaging plane", and to be transmitted through an imaged object to an x-ray detector array orientated within the imaging plane. The detector array is comprised of detector elements which each measure the intensity of transmitted radiation along a ray projected from the x-ray source to that particular detector element. The detector elements can be organized along an arc each to intercept x-rays from the x-ray source along a different ray of the fan beam. The intensity of the transmitted radiation is dependent on the attenuation of the x-ray beam along the ray by the imaged object.

The x-ray source and detector array may be rotated on a gantry within the imaging plane, around the imaged object, so that the fan beam intercepts the imaged object at different angles. At each angle, a projection is acquired comprised of the intensity signals from each of detector elements. The gantry is then rotated to a new angle and the process is repeated to collect a number of projections at different angles to form a tomographic projection set.

The acquired tomographic projection set is typically stored in numerical form for computer processing to "reconstruct" a slice image according reconstruction algorithms known in the art. The reconstructed slice images may be displayed on a conventional CRT tube or may be converted to a film record by means of a computer controlled camera.

In either emission or transmission computed tomography the detector array may be rectilinear rather than arcuate.

A typical computed tomographic study entails the imaging of a series of slices of an imaged object with the slices displaced incrementally along a z-axis perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, longer scan times increase the discomfort to the patient who must remain nearly motionless to preserve the fidelity of the tomographic reconstructions. Accordingly, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the gantry. Hereafter, it will be assumed that the CT systems discussed are equipped with slip rings or the equivalent to permit continuous rotation of over 360°.

The time required to acquire the tomographic data set is more difficult to reduce. Present CT scanners require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the rotation of the gantry. The combination of constant patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Continuous translation of the imaged object during scanning shortens the total scanning time required for the acquisition of a given number of slices by eliminating the length of time normally required for repositioning the patient between scans. However, helical scanning introduces certain errors with regard to the data in the acquired tomographic projection sets. The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object in the z-axis. The severity of the image artifacts depends generally on the "helical offset" in the projection data, measured as the absolute value of the difference between the table locations of the scanned data and the z axis value of the desired slice plane. Errors resulting from helical scanning will be referred to collectively as "skew" errors.

Several methods have been used to reduce skew errors in helical scanning. A first approach disclosed in U.S. Pat. No. 4,630,202 issued Dec. 16, 1986, reduces the pitch of the helical scan and then averages the projection data of consecutive 360° tomographic projection sets. The effect is equivalent to using a detector array with a larger width along the z axis, which also moves less in the z direction during a rotation of the gantry, i.e. with a lesser scanning pitch. Skew errors are reduced using this method, but at the expense of additional scanning time necessitated by the lower scanning pitch. Thus, this method reduces, to some extent, the advantages to be gained by helical scanning.

Skew errors at the ends of the tomographic projection set may be reduced in conjunction with this approach by changing the weighting of the last and first projections of the 360° tomographic projection set when it is "averaged" with other, consecutive 360° projection sets to give greatest weight to the data of the 360° projection closest to the slice plane.

A second approach disclosed in U.S. Pat. No. 4,789,929 issued Dec. 6, 1988, also applies weighting to the projections of combined, consecutive 360° tomographic projection sets, but the weighting is a function of the z-axis position of each projection for interpolation between 360° projection sets. This approach of interpolating over 720° generally increases partial volume artifacts. Partial volume artifacts are image artifacts arising when certain volume elements of the imaged object contribute to only some of the projections of the projection set.

A third approach, described in copending U.S. Pat. No. 5,046,003, entitled: "Method for Reducing Skew Image Artifacts in Helical Projection Scanning" and assigned to the same assignee as the present invention, uses non-uniform table motion to concentrate the helically acquired projections near the slice plane while limiting the accelerative forces on the patient.

SUMMARY OF THE INVENTION

The present invention reduces skew artifacts by applying a weighting function to the data of a helically acquired projection set, where the weighting function provides decreased weight to the projections furthest from the slice plane and increased weight to the projections closer to the slice plane. Thus the data with the greatest helical offset is de-emphasized, reducing image artifacts.

It is accordingly one object of the invention to reduce skew artifacts by weighting each projection according to its helical offset.

In one embodiment, the acquisition of data for the projection set is coordinated with the table motion so that the views of the projection set are centered about the slice plane with respect to the z-axis.

It is therefore another object of the invention to reduce skew artifacts by centering the projection set around the slice plane in addition to reducing the weighting of the projection data taken furthest from the slice plane. Centering the projection set around the slice plane reduces the maximum helical offset of any projection. Also, with the projection set centered about the slice plane, weighting de-emphasizes the data at each end of the projection set, thereby reducing motion induced artifacts per conventional underscan techniques.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
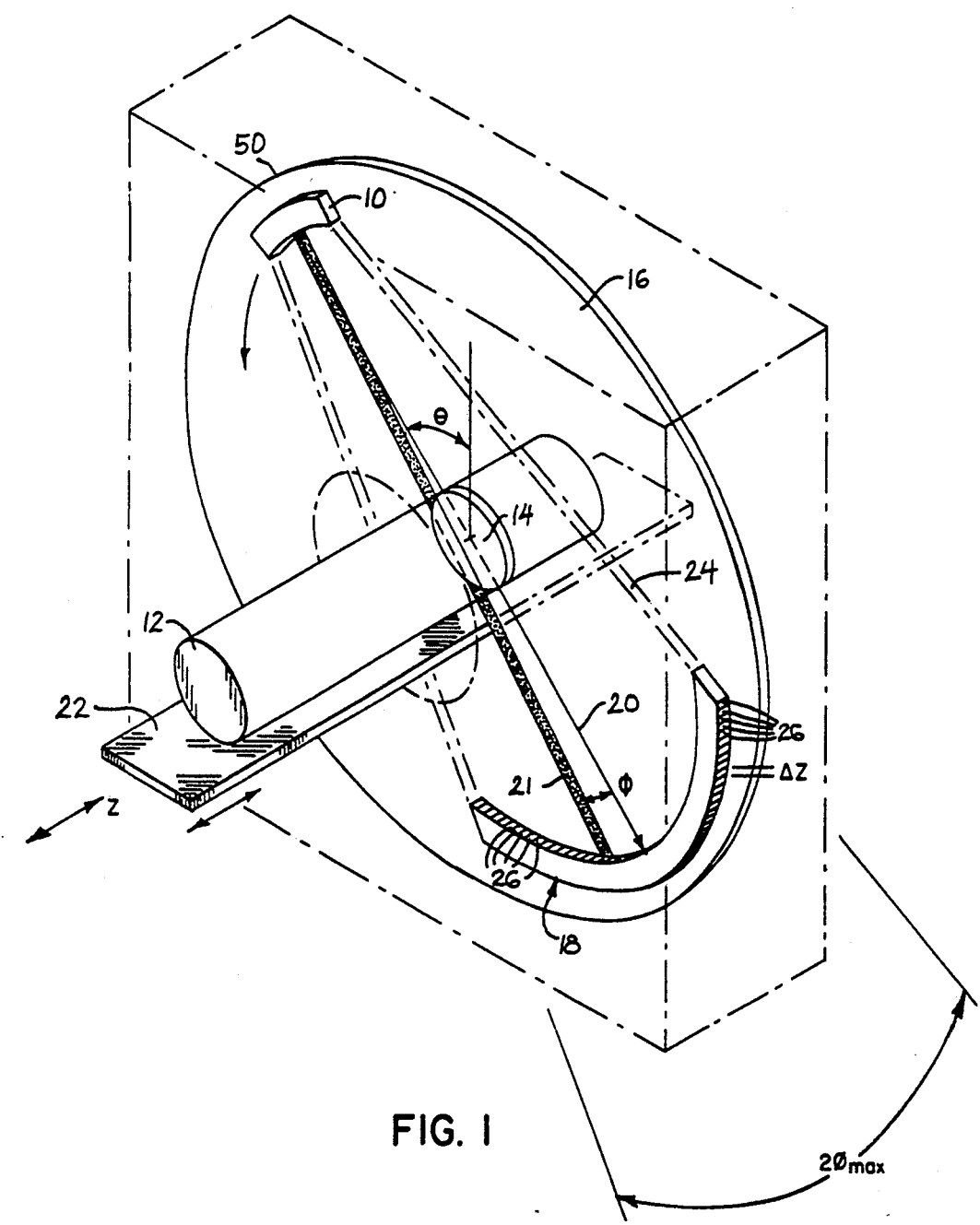
FIG. 1 is a pictorial representation of a CT apparatus including gantry, table and imaged object, and showing the relative angles and axes associated therewith.

Referring to FIG. 1, a CT gantry 16, representative of a "third generation" CT scanner includes an x-ray source 10 oriented to project a fan beam of x-rays 24 through imaged object 12 to detector array 18. The fan beam 24 is directed along an x-y plane of a Cartesian coordinate system, the "imaging plane", and subtends a "fan angle" of $2\phi_{max}$ as measured along the imaging plane. The detector array 18 is comprised of a number of detector elements 26 which together receive and detect a value proportional to the magnitude of a projected image resulting from the transmission of x-rays through the imaged object 12, or in the case of emission tomography, from the radiation emitted from the radiopharmaceutical isotopes within the imaged object 12. The angle $\phi$, measured from the centermost ray 20 of the fan beam 24, may identify each ray 21 of the fan beam 24 and its associated detector 26 and will be termed the fan beam angle.

The angular position $\theta$ of the gantry 16 with respect to the imaged object 12 is arbitrarily referenced to zero when the fan beam's center most ray 20 is vertical and directed downward. The gantry 16 is coupled to the gantry associated control modules 48, shown in FIG. 3 and to be described below, by means of slip rings 50 and is therefore free to rotate continuously through angles greater than 360° to acquire projection data.

The imaged object 12 rests on table 22 which is radiotranslucent so as to minimize interference with the imaging process. Table 22 may be controlled so that its upper surface translates along the z axis perpendicular to the x-y imaging plane, by moving the slice plane 14 defined with respect to the imaged object 12 across the imaging plane swept by the fan beam 24. For simplicity, it will be assumed henceforth that the table 22 moves at a constant velocity and therefore that the z axis position of the table 22 is proportional to the angular position $\theta$ of the gantry 16. Accordingly, the tomographic projections acquired may be defined either in terms of z or $\theta$.

Figure 2A:
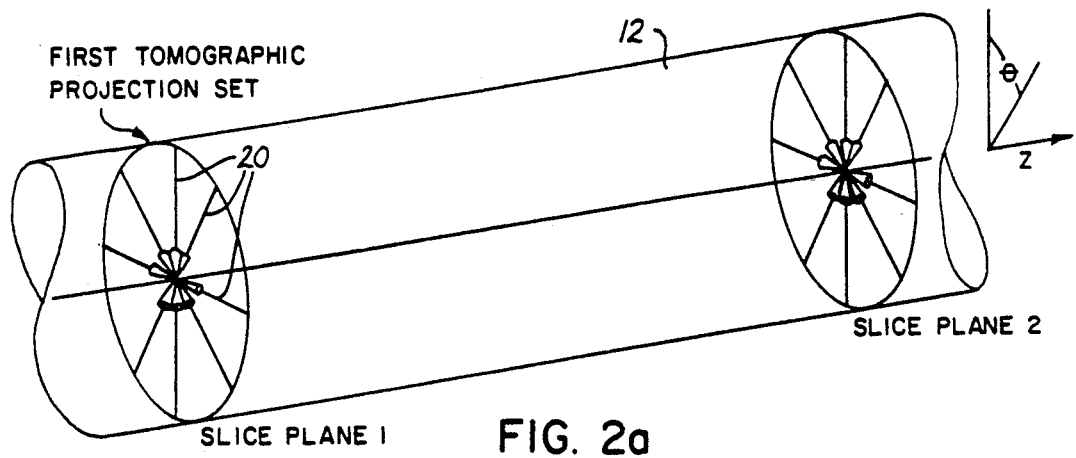
FIGS. 2(a) and 2(b) are schematic illustrations of the imaged object of FIG. 1 showing the relative orientation of the gantry and imaging plane with respect to the imaged object for constant z axis scanning and helical scanning respectively. The pitch of the helical scanning is exaggerated, for clarity.
Figure 2B:
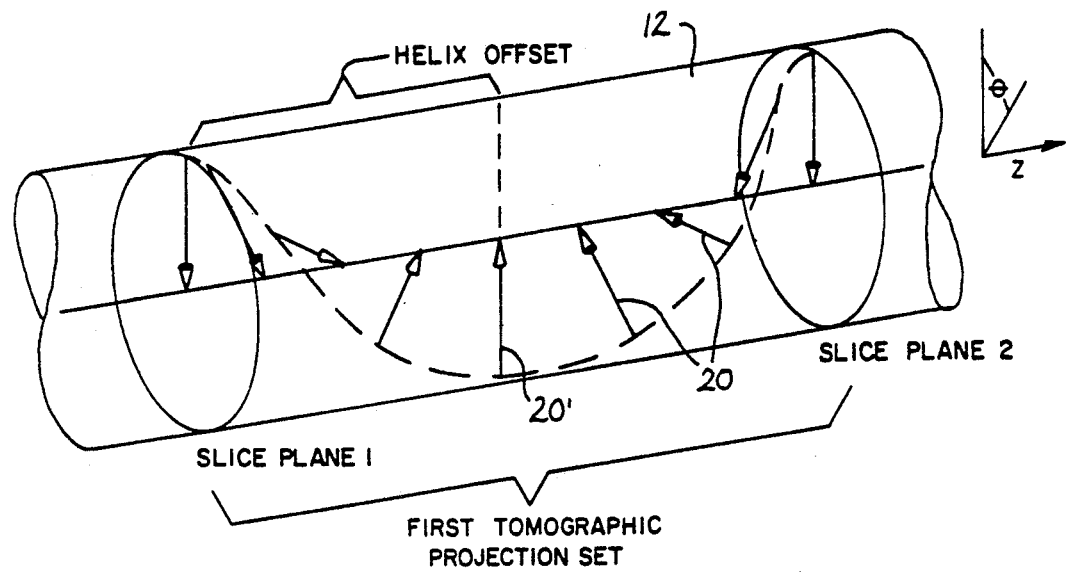

Referring to FIGS. 2(a) and 2(b), the angular position of the gantry and the z-axis position of the imaging plane with respect to the imaged object is shown by projection arrows 20 for a constant z-axis scan and a helical scan, respectively. In the constant z-axis scan, shown in FIG. 2(a) each tomographic projection set is acquired at a constant z-axis position and the imaged object is moved along the z-axis to the next slice plane between such acquisitions.

This differs from the helical scan in FIG. 2(b) where the z-axis position of the imaged object with respect to the imaging plane changes constantly during the acquisition of each tomographic projection set. Accordingly, arrows 20 trace a helix within the imaged object along the z-axis. The pitch of the helix will be referred to as the scanning pitch.

Figure 3:
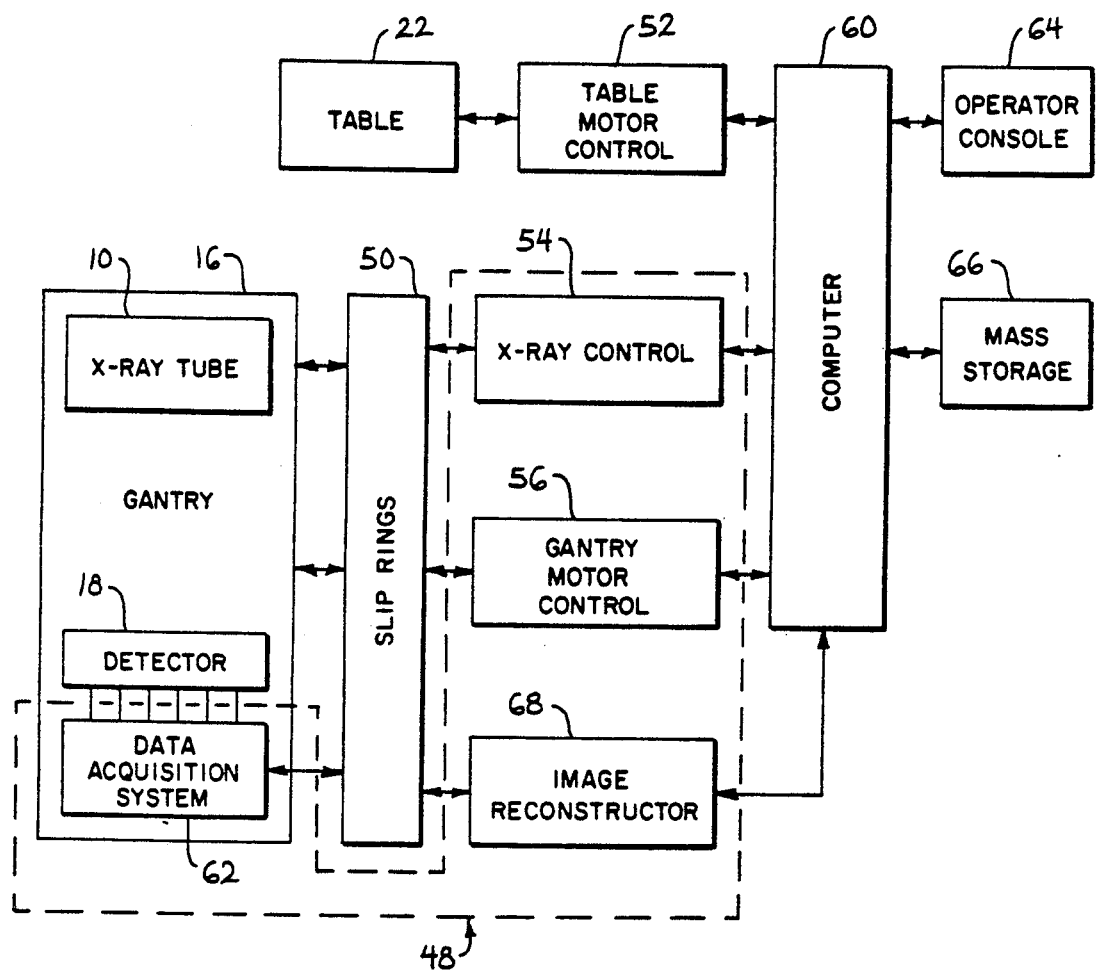
FIG. 3 is a block diagram of a CT control system that may be used with the CT apparatus of FIG. 1, and that is useful for practicing the present invention.

Referring now to FIG. 3, the control system of a CT imaging system suitable for use with the present invention has gantry associated control modules 48 which include: x-ray control 54 which provides power and timing signals to the x-ray source 10, gantry motor controller 56 which controls the rotational speed and position of the gantry 16 and provides information to computer 60, and data acquisition system 62, regarding gantry position, and image reconstructor 68 which receives sample and digitized signals from the detector array 18 via the data acquisition system 62 to perform high speed image reconstruction according to methods known in the art. Each of the above can be connected to its associated elements on the gantry 16 via slip rings 50 and serves to interface computer 60 to various gantry functions.

The speed and position of table 22 along the z-axis, is communicated to and controlled by computer 60 by means of table motor controller 52. The computer 60 receives commands and scanning parameters via operator console 64 which is generally a CRT display and keyboard which allows the operator to enter parameters for the scan and to display the reconstructed image and other information from the computer 60. A mass storage device 66 provides a means for storing operating programs for the CT imaging system, as well as image data for future reference by the operator.

Referring again to FIG. 1, a helical projection set is acquired by moving table 22 so as to pass a slice plane 14, identified with respect to the imaged object 12, past the imaging plane as the gantry is rotated through 360° to gather projections. Within this 360° of projection data, there is a duplication of data resulting from the equivalence in attenuation by the imaged object 12 along rays acquired at angles 180° apart.

Figure 4:
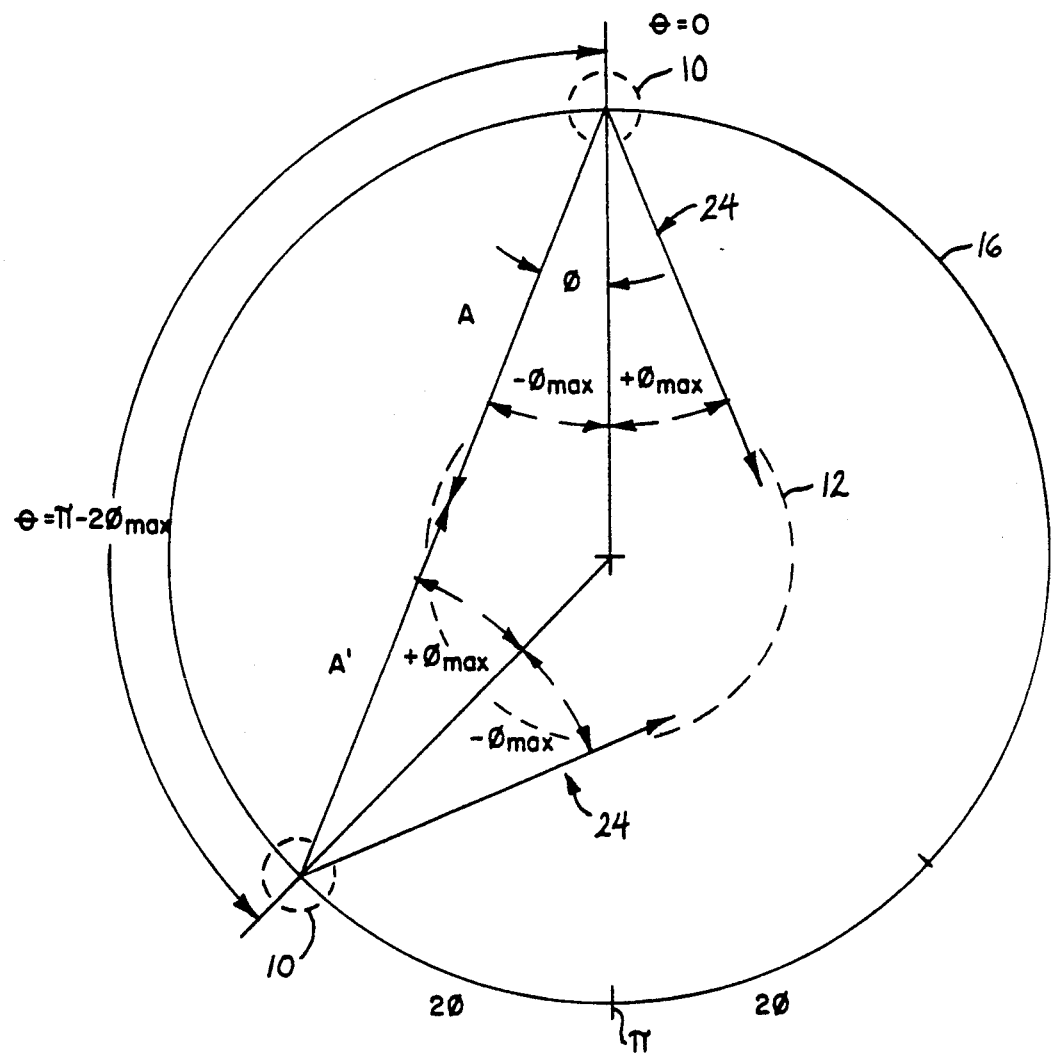
FIG. 4 is a diagram showing the geometry of an x-ray fan beam produced by the CT apparatus of FIG. 1 with the gantry shown positioned at two gantry angles $\theta$ as viewed along the z-axis.

The source of the duplicative data within 360° ($2\pi$ radians) of fan beam projection data may be demonstrated graphically. Referring to FIG. 4, a fan beam 24 at first gantry position $\theta=0$ includes ray A at angle $-\phi_{max}$ within the fan beam 24. The ray A is received by a detector element 26 (not shown) which produces a signal $P(\theta_1, -\phi_{max})$, where $\theta_1=0$, proportional to the line integral of the absorption of the x-ray radiation along ray A by imaged object 12. At a second fan beam 24 at second gantry position $\theta_2=\pi-2\phi_{max}$, it will be appreciated that the same line integral absorption measured along ray A in the first gantry position, is also measured along ray A' in the second gantry position, where ray A' is at angle $+\phi_{max}$ within the fan beam 24. The x-ray along ray A' is received by a detector element 26 (not shown) which produces a signal $P(\theta_2, \phi_{max})$. The identity of the measurements along ray A and A' may be generalized by the following relationship:

$$P(\theta, 100) = P(\theta + \pi + 2\phi, -\phi) \tag{1}$$

where $\theta$ and $\phi$ are any gantry angle and any fan beam angle respectively.

It should be noted that in the case of helical scanning, pairs of duplicative data may not have the same value because of the motion of the table 22 and of the imaged object 12 as the gantry rotates. Duplicative data having different values as a result of helical scanning will be termed "redundant" data.

Figure 5A:
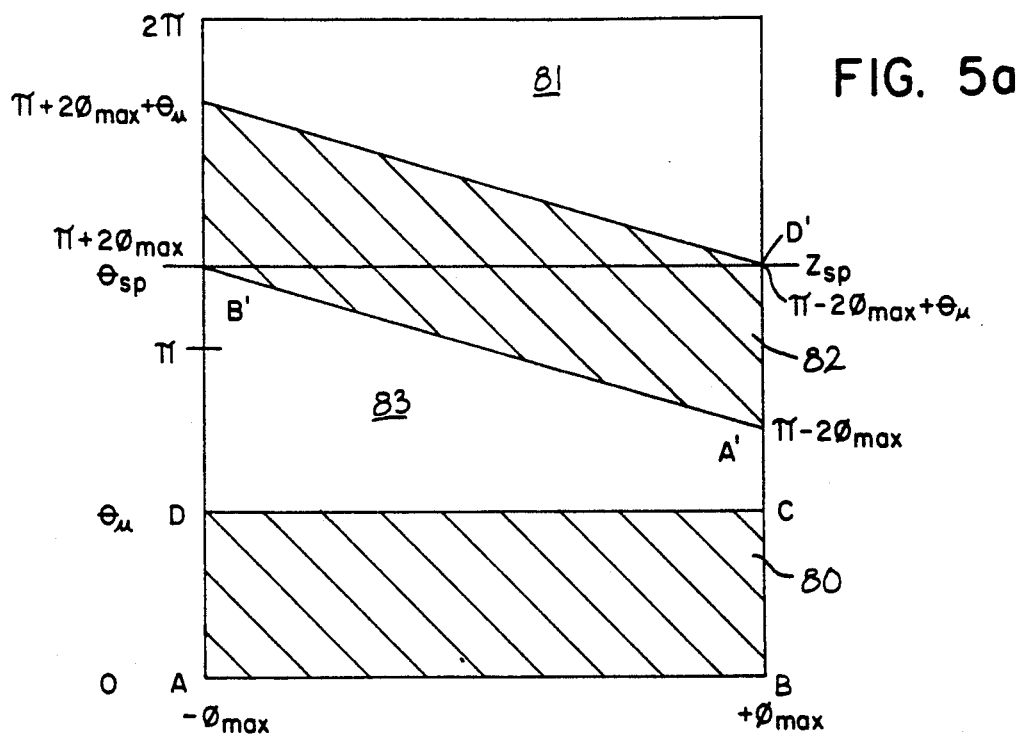
FIG. 5(a) is a graphical representation of the arguments $\theta$ and $\phi$ associated with $2\pi$ radians of projection data where the data is not centered about the slice plane, showing the weighting of that data.

Referring to FIG. 5(a), the arguments $\theta$ and $\phi$ for the data comprising a helical projection set may be shown schematically. Horizontal lines represent projections taken at a constant gantry position $\theta$ and include detector signals from angles $\phi$: $-\phi_{max} < \phi < +\phi_{max}$. The gantry angle $\theta$ of the projection along line AB is arbitrarily assigned to 0 and is the first projection of helical projection set. Successive projections are acquired at increasing gantry angles $\theta$ up to $\theta = 2\pi$ radians while the table 22 is advanced along the z-axis, per helical scanning techniques discussed above.

As a result of the table motion during the scanning process, the projection data associated with each gantry angle $\theta$ also corresponds to a unique table position z. By definition, at $\theta = \theta_{sp}$, the slice plane 14 of the imaged object 12 is aligned with the imaging plane and the helical offset is zero. For gantry angles greater or less than $\theta_{sp}$, the imaging plane diverges from the slice plane 14 and the helical offset of the projection data increases. The greatest helical offset is for those projection acquired at gantry angles furthest from $\theta_{sp}$.

Image artifacts, produced by data with substantial helical offset, may be reduced by applying a weighting factor to this offset data to decrease its contribution to the final image. A second weighting factor must be then applied to the data redundant to this data, to avoid new weighting-induced image artifacts.

For example, if the slice plane 14 is aligned with the imaging plane for $\theta = \pi + 2\phi_{max}$, as shown in FIG. 5(a), then the data of region 80, for $0 < \theta < \theta_u$ where $\theta_u$ is a predetermined value chosen to be less than $\pi - 2\phi_{max}$, encompasses an area of large helical offset. In this embodiment $\theta_u$ is chosen to be 45°, however other values may be chosen that balance increased artifact reduction with corresponding increased image noise as $\theta_u$ is increased. Weights $w_1$ are applied to the data of region 82. The redundant data for region 80, per equation (1) above, is contained in region 82 where $\pi - 2\phi < \theta < \pi + 2\phi + \theta_u$. Compensating weights $w_3$ are applied to this region. The remaining regions designated region 81 and region 83 and containing data that is "non-redundant" with respect to region 80 are given weights $w_2$. Generally, weights produced by any weighting function $w(P)$ may be chosen so long as for any two redundant points $P_1$ and $P_3$ and non-redundant point $P_2$:

$$w(P_1) + w(P_3) = 2w(P_2) \text{ and} \tag{2}$$

$$w(P_1) < w(P_3) \tag{3}$$

where $P_1$ is from a projection with higher helical offset than the projection of $P_3$.

It should be recognized that the definition of redundancy is relative and that for any first region covering less than half of the $2\pi$ projection set a second redundant region may be identified. Accordingly, the slice plane 14 may be chosen after the data has been acquired and appropriate weighting determined based on the areas of the projection set that have the most helical offset. In a second embodiment, therefore, the slice plane 14 is chosen before the acquisition of data and thus may be optionally centered within the projection set.

Figure 5B:
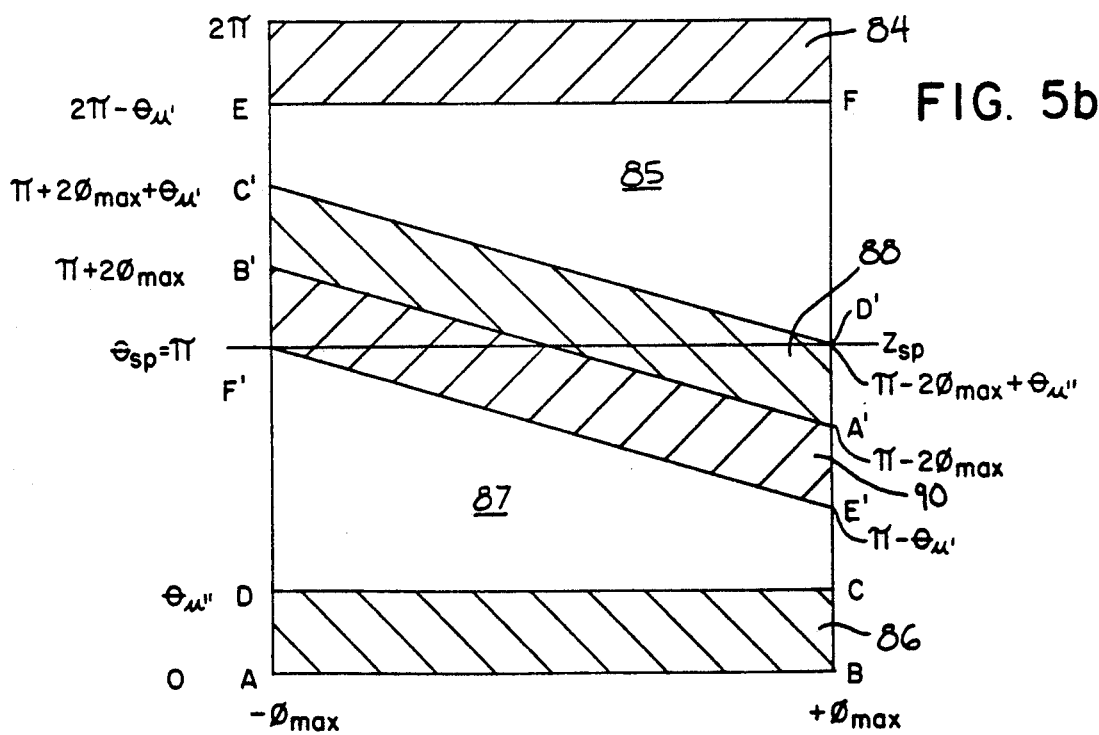
FIG. 5(b) is a graphical representation similar to that of FIG. 5(a), where the data is centered about the slice plane, and showing the weighting of that data.

Referring to FIG. 5(b), the acquisition of data is coordinated with the motion of the table so that the slice plane 14 crosses the image plane when $\theta = \pi$ and $\theta$ is arbitrarily referenced to 0 at the beginning of the scan. The regions of maximum helical offset are symmetric about the slice plane 14 and shown as regions 86 and 84 where $0 < \theta < \theta_{u''}$ for region 86, and $2\pi - \theta_{u'} < \theta < 2\pi$ for region 84, where $\theta_{u''}$ and $\theta_{u'}$ are any number of projections $\theta_{u''} < \pi - \theta_{u'}$ and $\theta_{u'} > \pi + 2\phi_{max} + \theta_{u''}$. These areas are given a reduced weighting function. Redundant regions 88 and 90, per equation 1 above are given an increased weighting function. Again, $\theta_{u'}$ and $\theta_{u''}$ are chosen to balance the concerns of artifact reduction and image noise toleration.

Centering the slice plane 14 produces several benefits. First, the maximum helical offset is reduced. Also, to the extent that the image artifacts may not be linearly related to helical offset, the image artifacts will be further reduced over those of the previous embodiment. Second, discontinuities caused by other motion artifacts, such as respiratory motion, to the extent that such discontinuities tend to be concentrated at the ends of the projection set, will be reduced.

Figure 6:
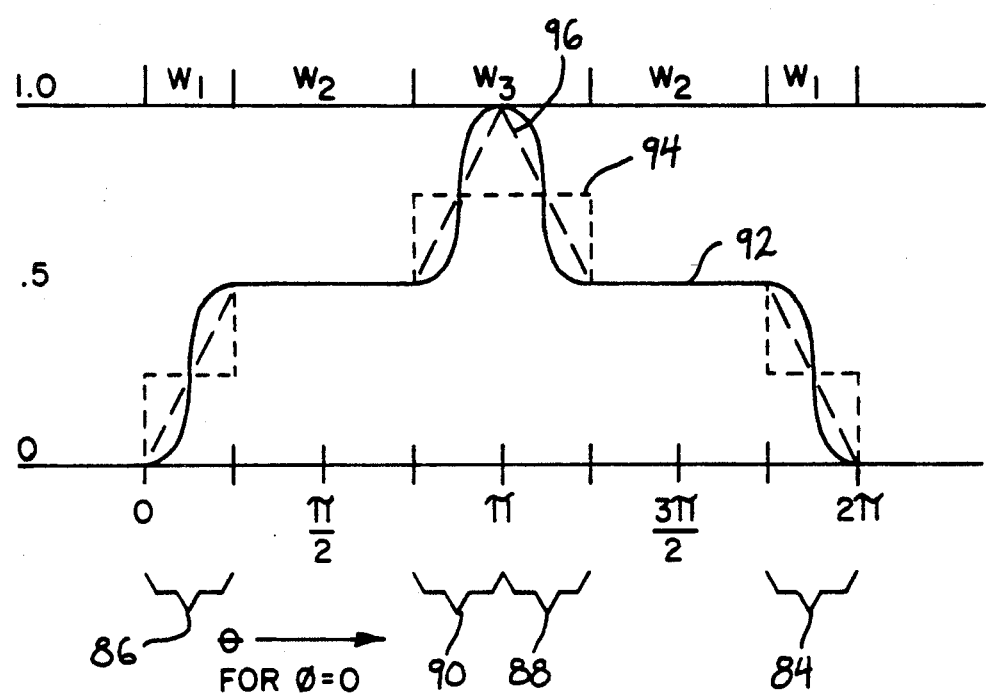
FIG. 6 is a graphical representation of three weighting functions, as taken along $\phi=0$, that may be applied to the projection data of FIG. 5(b).

Referring to FIG. 6, several weighting functions for the projection set shown in FIG. 5(b) are given which satisfy the conditions of equations 2 and 3 above. For example, the weighting function may be a linear function of $\theta$, as depicted by curve 96 or a cubic function of $\theta$ as depicted by curve 92. The latter cubic weighting function, based on the equation $3x^2 - 2x^3$, is most effective because its first derivative is zero at the boundaries of the regions where it is applied. A piecewise constant weighting function shown by curve 94 performs a simple average of the redundant regions and thereby offers the least degradation in signal-to-noise ratio. In weighting function 96 and 92 the signal-to-noise ratio is somewhat lower.

Weighting methods for projection sets, as are known in the art, are taught generally in U.S. Pat. No. 4,580,219 ('219) entitled: "Method for Reducing Image Artifacts Due to Projection Measurement Inconsistencies" issued to the same assignee as the present invention and hereby incorporated by reference. The '219 patent discloses a method for decreasing the relative weighting of the end projections of the projection set to decrease artifacts produced by the motion of the imaged object. The present invention differs in that it applies the reduced weights to the projections with the most helical offset, which as discussed, may or may not be the end projections.

Many modifications and variations of the preferred embodiment which will still be within the spirit and scope of the invention will be apparent to those with ordinary skill in the art. For example, weighting may also be applied to the "non redundant" data according to its degree of helical offset to further reduce image artifacts. Also the slice plane 14 may be positioned anywhere within the projection set with appropriate changes in the weighted regions.

We claim:

1. A method of producing a tomographic image of an imaged object from projection data acquired in a helical scan, the data derived from a series of fan beam projections at a plurality of gantry angles $\theta$ about a z axis and having a helical offset along the z axis, the fan beam projections subtending an angle $2\phi_{max}$, comprising the steps of:
   a) acquiring a series of projections over 360° of gantry angles $\theta$ as the imaged object is translated along the z axis, the projections indicating the attenuation of energy by the imaged object along a fan beam plane;
   b) reducing the relative contribution of a first set of data in the projection set having helical offset of greater than a predetermined value;
   c) increasing the relative contribution of a second set of data in the projection set redundant with the first set of data; and
   d) reconstructing a tomographic image from the first and second data set and the remaining data of the projection set.

2. The method of claim 1 where the step of reducing comprises assigning a weighting factor to the projection data wherein said weighting factor decreases monotonically as a function of helical offset.

3. The method of claim 1 where the step of reducing comprises assigning a weighting factor to the projection data wherein said weighting factor is a cubic function of helical offset.

4. The method of claim 1 where the step of reducing comprises assigning a weighting factor to the projection data wherein said weighting factor is a piecewise continuous function of helical offset.

5. A method of producing a tomographic image of an imaged object from projection data acquired in a helical scan, the data derived from a series of fan beam projections at a plurality of gantry angles $\theta$ about a z axis and having a helical offset along the z axis, the fan beam projections subtending an angle $2\phi_{max}$, comprising the steps of:
   a) identifying a slice plane $z_{sp}$ relative to the imaged object and parallel to the image plane;
   b) moving the imaged object along the z-axis and rotating the gantry so that the imaging plane crosses the slice plane at a gantry angle of 180° and acquiring a series of projections over 360° of gantry angles $\theta$, including a first and a last projection, the projections indicating the attenuation of energy by the imaged object along a fan beam plane;
   c) reducing the relative contribution of a first set of data in the projection set having helical offset of greater than a predetermined value;
   d) increasing the relative contribution of a second set of data in the projection set redundant with the first set of data; and
   e) reconstructing a tomographic image from the first and second data set and the remaining data of the projection set.

6. The method of claim 5 wherein the first set of data comprises two distinct regions, one including the first projections of the projection set and the other including the last projections of the projection set.

7. The method of claim 6 wherein the data of the two distinct regions are symmetrically disposed about the slice plane.

* * * * *

UNITED STATES PATENT AND TRADEMARK OFFICE
CERTIFICATE OF CORRECTION

PATENT NO. : 5,170,346
DATED : December 8, 1992
INVENTOR(S) : Crawford et al.

It is certified that error appears in the above-identified patent and that said Letters Patent is hereby corrected as shown below:

Col. 6, line 11     "$P(\Theta, 100) = P(\Theta + \pi + 2\phi, -\phi)$" should be --$P(\Theta, \phi) = P(\Theta + \pi + 2\phi, -\phi)$.

Signed and Sealed this

Fourteenth Day of December, 1993

Attest:

BRUCE LEHMAN

Attesting Officer     Commissioner of Patents and Trademarks